United States Patent
Reimels et al.

[19]

[11] Patent Number: 5,910,148
[45] Date of Patent: Jun. 8, 1999

[54] SUTURE RETROGRADER

[75] Inventors: William J. Reimels, Scituate; Richard F. Wenstrom, Jr., Norwood, both of Mass.

[73] Assignee: Mitek Surgical Products, Inc., Westwood, Mass.

[21] Appl. No.: 08/907,223

[22] Filed: Aug. 6, 1997

[51] Int. Cl.⁶ .................................................. A61B 17/04
[52] U.S. Cl. ........................... 606/144; 606/139; 606/148
[58] Field of Search ...................... 606/144, 148, 606/205, 206, 207, 222, 224, 225, 211, 139

[56] References Cited

U.S. PATENT DOCUMENTS

| | | | |
|---|---|---|---|
| 4,779,616 | 10/1988 | Johnson | 128/334 |
| 5,250,054 | 10/1993 | Li | 606/148 |
| 5,364,410 | 11/1994 | Failla et al. | 606/148 |
| 5,447,512 | 9/1995 | Wilson et al. | 606/139 |
| 5,496,335 | 3/1996 | Thomason et al. | 606/148 |
| 5,499,991 | 3/1996 | Garman et al. | 606/148 |
| 5,501,692 | 3/1996 | Riza | 606/148 |
| 5,562,685 | 10/1996 | Mollenauer et al. | 606/144 |
| 5,569,269 | 10/1996 | Hart et al. | 606/144 |
| 5,573,542 | 11/1996 | Stevens | 606/144 |
| 5,643,292 | 7/1997 | Hart | 606/144 |
| 5,653,716 | 8/1997 | Malo et al. | 606/139 |
| 5,658,299 | 8/1997 | Hart | 606/139 |
| 5,772,672 | 6/1998 | Toy et al. | 606/139 |

*Primary Examiner*—Michael Buiz
*Assistant Examiner*—Julian W. Woo
*Attorney, Agent, or Firm*—Nutter, McClennon & Fish, LLP

[57] ABSTRACT

A device for grasping sutures includes an elongate housing and a hollow introducer needle attached to a distal end of the housing. The introducer needle has an open distal end having a sharpened, tissue penetrating edge. A suture grasping element is disposed in the open distal end of the introducer needle and is movable at least between first and second positions corresponding to the retracted and extended positions of the suture grasping element, respectively. The suture grasping element may consist of two jaws, one jaw having a pod located on a distal end thereof and one jaw being movable between opened and closed positions. In the closed position, the pod contacts a distal portion of the other jaw in a manner sufficient to retain a suture between the jaws. In additional embodiments, the suture grasping element may also consist of a substantially diamond-shaped wire loop or two wire-like member.

26 Claims, 9 Drawing Sheets

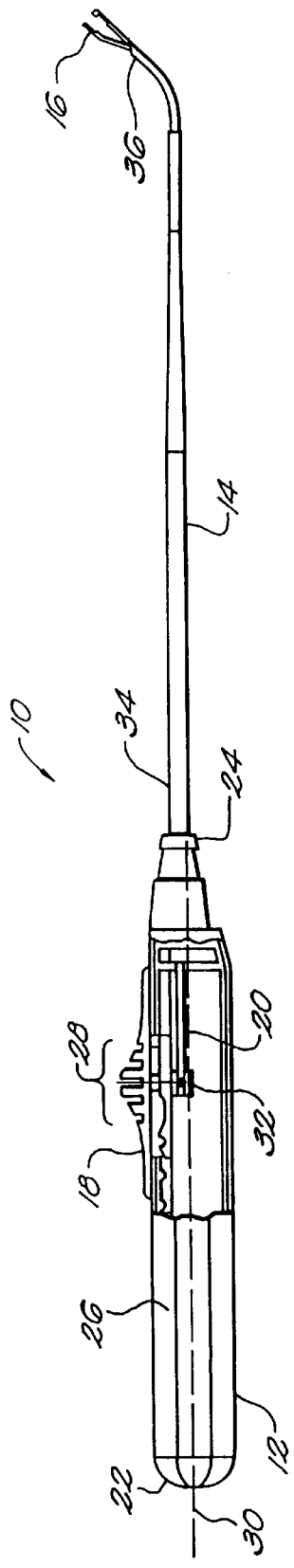
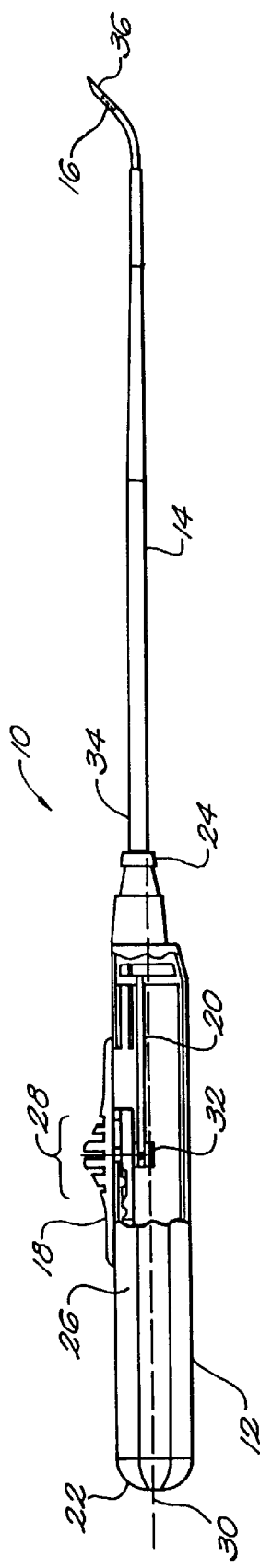
FIG. 1
FIG. 2

SUTURE RETROGRADER

FIELD OF THE INVENTION

The invention relates to surgical instruments for grasping a suture or similar ligature within a patient's body. More particularly, the invention relates to suture grasping devices suitable for grasping a length of suture and drawing or pulling the suture through tissue in either open or closed surgical settings.

BACKGROUND OF THE INVENTION

A variety of devices and methods for grasping free suture portions or passing suture material through tissue are known in the art.

One method for passing a suture end through tissue involves attaching the suture end to a needle. The needle can then be passed through the tissue using a needle manipulating device. Once passed through the tissue, a separate device, known as a retrograder, may be employed to retrieve or otherwise manipulate the needle and suture.

In other methods, sharpened needle tips having suture grasping structures located within or near the needle tip may be used to grasp a suture, then penetrate the tissue to leave the suture end on the far side of the tissue where it can be grasped for further manipulation. Or, such a device may be used to penetrate the tissue first, grasp a suture on the far side of the tissue, and pull the suture back through the tissue.

The suture grasping elements employable in such devices can have various configurations. U.S. Pat. No. 5,569,261 discloses the use of two wire-like elements, one of which has a hook-shaped configuration. U.S. Pat. No. 5,496,335 discloses a suture grasping element having forcep jaws with sharpened tips. U.S. Pat. No. 5,501,692 discloses a suture grasping element in the form of a looped wire.

The known devices suffer from some drawbacks. In closed surgery, especially in arthroscopic surgery involving a joint such as a knee or shoulder, space and visibility constraints at the surgical site render it difficult to fully extend a suture grasping device to easily grasp a suture. Thus, it can be difficult to locate and grasp a portion of a suture during closed surgical procedures using the above described devices.

Also, because many of these devices have sharp edges that help to grasp the suture, there is a risk that the suture material will be cut while performing the desired suture manipulation at the surgical site.

SUMMARY OF THE INVENTION

The present invention provides a device for grasping sutures. The device of the invention has an elongate housing and a hollow introducer needle attached to a distal end of the housing. The introducer needle has an open distal end that includes a sharpened, tissue penetrating edge. A suture grasping element is disposed in the open distal end of the introducer needle. An actuator element, provided on a side wall of the housing, is connected to the suture grasping element through a lining member.

The connection between the actuator and the suture grasping element is such that movement of the actuator effects movement of the suture grasping element between positions in which it is extended from and retracted within the needle. The actuator is movable between retracted and extended positions of the suture grasping element, respectively. An intermediate position may also be provided for the actuator, corresponding to a partially extended position of the suture grasping element.

In one embodiment, the suture grasping element comprises two jaws. A first jaw includes a pod located on a distal end thereof, while a second jaw is movable between opened and closed positions. In the closed position, the pod contacts a distal portion of the second jaw in a manner sufficient to retain a suture between the jaws.

In another embodiment, the suture grasping element comprises a compressible, substantially diamond-shaped wire loop. This structure is also movable among extended, partially retracted, and fully retracted positions. When the actuator is moved from the extended position to the intermediate position, the wire loop compresses and is partially retracted into the inner bore of the introducer needle. In this position, a portion of the loop that is effective to retain a suture remains extended from the introducer needle.

In still another embodiment, the suture grasping element consists of two wire-like members with at least one of the members having a substantially transverse hook formed on its distal end. In the extended position, the distal portions of the wire-like members are spaced apart. As the actuator is moved to the intermediate position, the substantially transverse hook contacts the other wire-like members so as to form a closed region between the members capable of slidably retaining a suture.

The introducer needle may be oriented at a variety of angles with respect to a longitudinal axis of the housing.

BRIEF DESCRIPTION OF THE DRAWINGS

The invention will be more fully understood by reference to the following detailed description when considered in conjunction with the accompanying drawings, in which:

FIG. 1 is an elevated view with a partial cut-away of a suture retrograder of the invention illustrating an open, fully extended suture grasping element;

FIG. 2 is an elevated view with a partial cut-away of the suture retrograder of FIG. 1, illustrating the suture grasping element in a fully retracted, closed position;

DETAILED DESCRIPTION OF THE INVENTION

Figure 3:
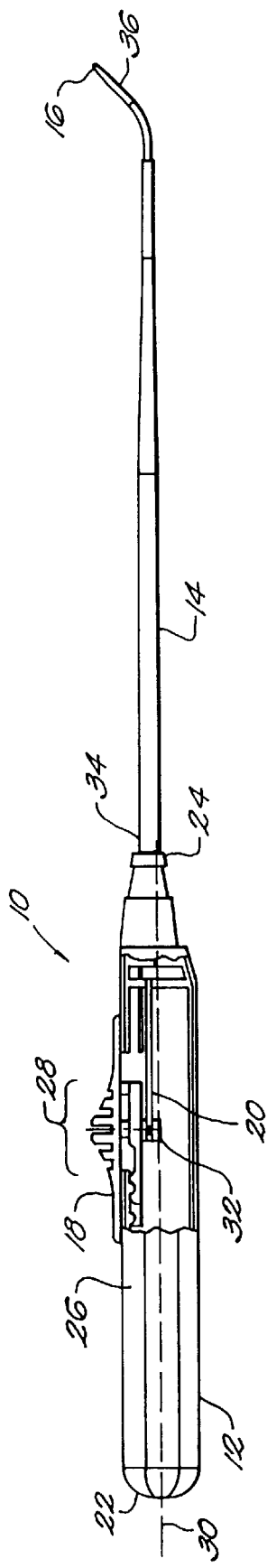
FIG. 3 is an elevated view, with a partial cut-away, of the suture retrograder of FIG. 1 showing the suture grasping element in a partially retracted, intermediate position.

A surgical device 10 of the invention for grasping or retrograding a suture or other ligature is illustrated in FIG. 1. This exemplary instrument includes a housing 12, a hollow introducer needle 14, a suture grasping element 16, an actuator 18 and a linking member 20 which connects the actuator 18 to the suture grasping element 16.

The exemplary housing 12 is elongate, generally cylindrical and has opposed proximal 22 and distal 24 ends. The shape and dimensions of the housing may be selected by a person of ordinary skill in the art to allow the housing to be suitably grasped by a surgeon in an operating environment.

The actuator 18 is slidably mounted on a side wall 26 of the housing 12. In the embodiment shown in FIG. 1, the actuator has a rectangularly-shaped base and includes a series of flanges 28 having varying heights and angled surfaces so as to be easily manipulated in either of two directions by a surgeon's thumb. The actuator 18 is mounted so as to slide in a direction substantially parallel to a longitudinal axis 30 of the housing 12. The actuator 18 is movable between a first position (shown in FIG. 2), wherein the actuator 18 is closest to the proximal end 22 of the housing 12, and a second position (shown in FIG. 1), wherein the actuator 18 is closest to the distal end 24 of the housing 12. The actuator may also be selectively positionable at locations between the first and second positions as illustrated in FIG. 3.

The actuator 18 communicates with the interior of the housing 12 through a transverse member 32. The transverse member 32 may extend through a rectangular slot (not shown) in the side wall 26 of the housing 12 along which the actuator 18 slides.

The transverse member 32 of the actuator 18 is connected to the linking member 20, which may be a rigid or semi-rigid rod. Preferably, the linking member 20 extends from the transverse member 32 in the interior of the housing 12 through the interior of the hollow introducer needle 14 to communicate with the suture grasping element 16.

Figure 4:
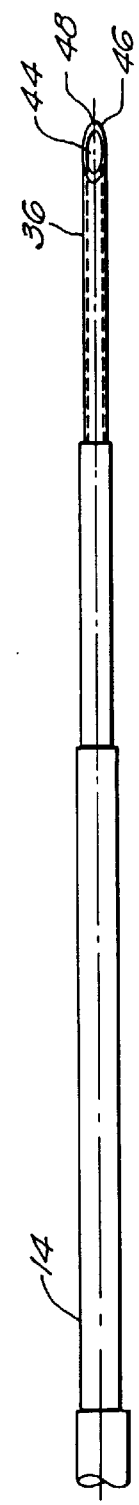
FIG. 4 is a view of the introducer needle portion of the suture retrograder of FIG. 1, rotated 90°.

As shown in FIG. 4, the distal end 36 of the introducer needle 14 has an opening 44, which communicates with the interior of hollow introducer needle 14. The edges of the open distal end 46 are sharpened, coming to a point 48 at the distal-most edge. The open distal end 44 is thus suited to penetrate tissue. The hollow introducer needle 14 has a proximal end 34, which is connected to the distal end 24 of the housing 12, and a distal end 36.

Figure 5:
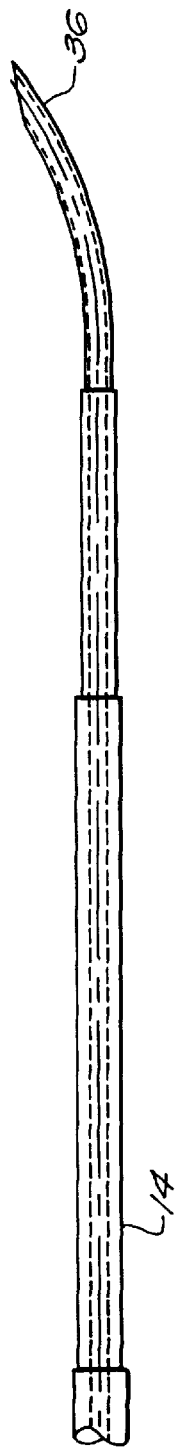
FIG. 5 is an elevated view of one embodiment of an introducer needle portion of a suture retrograder constructed according to the present invention.

The distal end 36 of the introducer needle may extend at various angles. For example, as shown in FIG. 1, the distal end 36 of the introducer needle 14 is angled approximately 60° with respect to the longitudinal axis 30 of the housing 12. The distal end 36 of the introducer needle 14 may take on other configurations as well, such as a 30° curved distal end 36 (FIG. 5), or a curved distal end 36 taking the shape of a hook (FIGS. 6 and 7).

Figure 6:
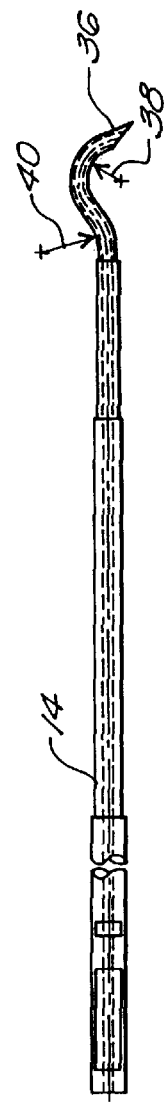
FIG. 6 is an elevated view of another embodiment of an introducer needle portion of a suture retrograder in a partially formed state.
Figure 7:
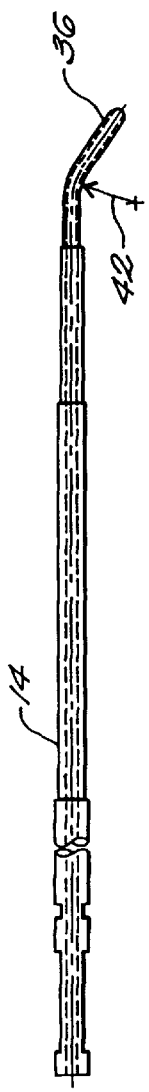
FIG. 7 is a view of the introducer needle of FIG. 6, fully formed and rotated 90°.

A hook-shaped distal end 36 may be formed as shown in FIGS. 6 and 7. As illustrated in FIG. 6, the hook shape may be formed by creating a first curve 38 in the distal-most region of the introducer needle. A second curve 40 is formed proximally to the first curve 38, in the same plane as the first curve 38, but in the opposite direction from the first curve 38. Referring to FIG. 7, wherein the needle of FIG. 6 is rotated 90°, the hook is provided with a curve 42 in a third direction which is in a plane perpendicular to the plane in which the first 38 and second 40 curves are formed.

FIGS. 8 through 17 illustrate various embodiments and positions of suture grasping elements useful with the suture retrograder of the invention.

Figure 8:
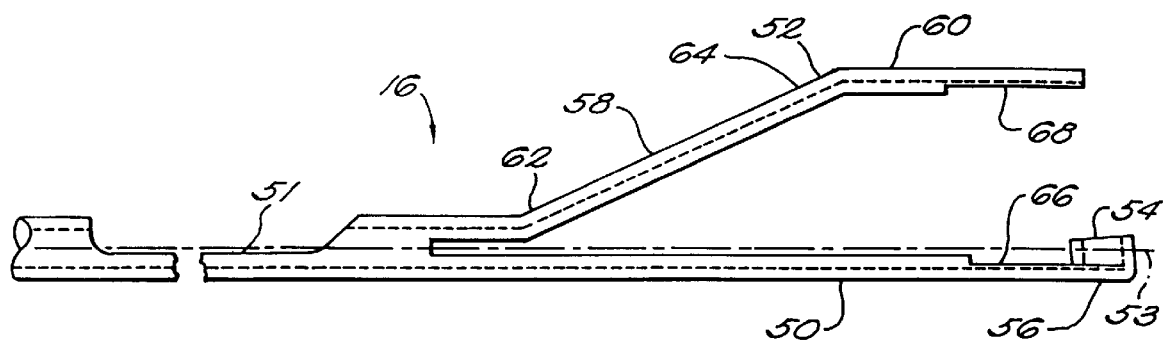
FIG. 8 is an elevated view of an open, extended suture grasping element having two jaw elements according to one embodiment of the invention.

A suture grasping element 16 having a first jaw 50 and a second jaw 52 is illustrated in FIG. 8. The first jaw 50 is substantially straight and has a pod 54 located on its distal end 56. The exemplary pod 54 is a cylindrical structure which extends from the first jaw 50 toward the second jaw 52. Generally, the pod 54 may have a height of about 0.010 to 0.100 inch, and preferably about 0.020 inch. In practice, the pod may be provided on either or both jaws.

The second jaw 52 includes at least two segments 58, 60. The first, angled segment 58 angles away from the first jaw 50. Accordingly, the first segment 58 has a proximal end 62 which is in proximity to the first jaw 50, and a distal end 64 which is spaced apart from the first jaw 50. The angle between the first segment 58 and the first jaw 50 is preferably in a range between about 15° and 45°. In the exemplary embodiment of FIG. 8, the first segment 58 is linear and forms an angle of approximately 25° with the first jaw 50. It will be understood, however, that other second jaw 52 configurations may be used within the scope of the invention.

The second segment 60 of the second jaw 52 extends distally from the first segment 58 and is therefore spaced apart from the first jaw 50. In the exemplary embodiment of FIG. 8, the second segment 60 is substantially linear and substantially parallel to the first jaw 50. Accordingly, the second segment 60 is spaced apart from the first jaw 50 along its length. The spacing between the pod 54 and the second segment 60 is generally in the range of about 0.020 to 0.250 inch, and is most preferably about 0.100 inch. The spaced-apart position of the first 50 and second 52 jaws as shown in FIG. 8 is referred to herein as the "open" position. The flexible suture grasping element 16 is biased to the open position and achieves that position when the suture grasping element 16 is fully extended from the introducer needle 14.

Recessed regions 66, 68 may be provided on the first 50 and second 52 jaws, respectively. Recessed region 68 on the second jaw 52 is located at the distal end of the second segment 60 and extends proximally over approximately half the length of the second segment 60. Recessed region 66 on the first jaw 52 is provided adjacent to the pod 54. The recessed regions 66, 68 are arranged to provide an area wherein, when the jaws 50, 52 are pushed together (the "closed" position), a suture may be slidably retained.

The suture grasping structure 16 may be made from any flexible material suitable for surgical use including metals such as stainless steel or super elastic nickel-titanium (Nitinol) or plastic materials having elastic properties such as polyester, polypropylene or nylon. In the exemplary embodiment of FIG. 8, the suture grasping structure 16 is formed from nickel-titanium tubing. The suture grasping structure 16 may also include a cut-out portion 51 wherein approximately half of the flexible tubing is cut away. The cut-out portion 51 preferably corresponds to a region of the flexible tubing that travels within the curved distal portion 36 of the introducer needle 14.

Figure 8A:
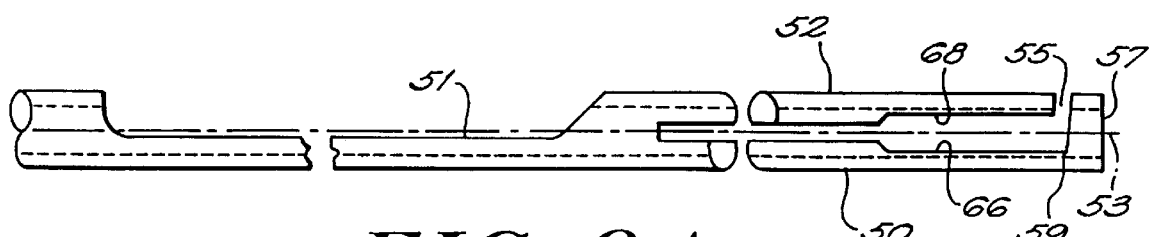
FIG. 8A is an elevated view of the suture grasping element of FIG. 8 in a partially formed state.

The jaws 50, 52 preferably are formed from a single piece of tubing. In such an embodiment, the pod 54 may also be integrally formed from the same piece of tubing. FIG. 8A illustrates the formation of the jaws 50, 52 and the pod 54 from a single piece of hypodermic needle tubing. In the stage of formation shown, the tubing has been machined, preferably by electric discharge machining ("EDM"), horizontally along the longitudinal axis 53 to separate two tines corresponding the first 50 and second 52 jaws, and to create the recessed regions 66, 68. The second jaw 52 may be fully formed by bending the tine corresponding to second jaw 52 into the form shown in and described with respect to FIG. 8.

A vertical cut 55 is also made in the tubing to separate a tubular portion 57 corresponding to the distal pod 54. This tubular portion 57 may be formed into the distal pod 54 shown in FIG. 8 by rotating the tubular portion 57 approximately 90° in a counter-clockwise direction about the point 59. Preferably, the vertical cut 55 is angled by approximately 5° so that the tubular portion may be rotated slightly more than 90°.

Figure 8B:
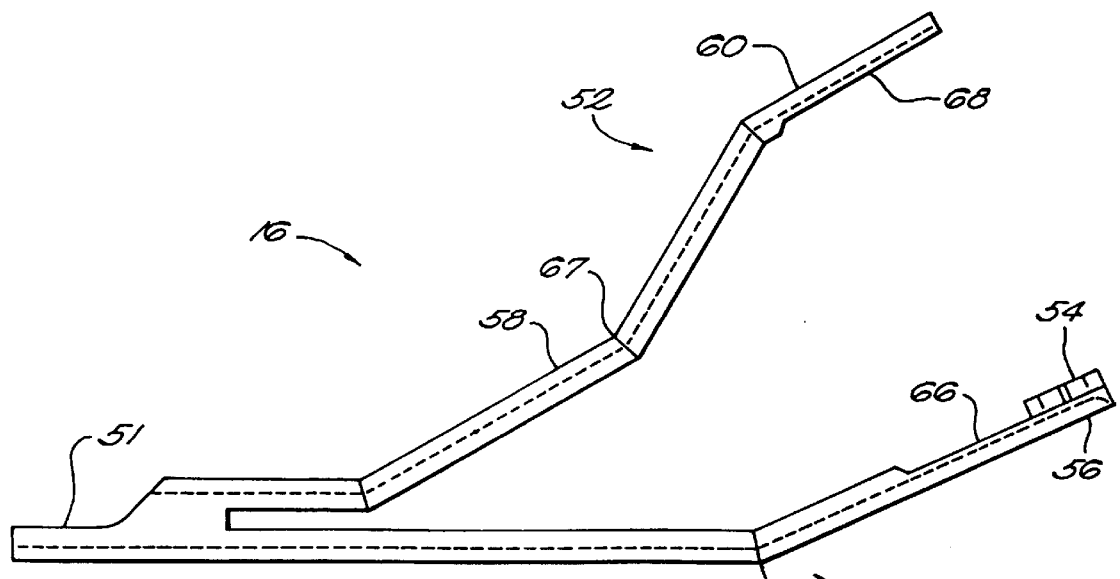
FIG. 8B is an elevated view of an open, extended suture grasping element having two jaws with additional angles.

The two-jawed suture grasping device 16 of FIG. 8 may also be formed with additional angles 67, 69 as shown in FIG. 8B. Angle 67 is provided in the first segment 58 of the second jaw 52 and angle 69 is provided in the first jaw 50. Generally, the angles are oriented in the same direction and may range from about 10° to 60°. Furnishing the jaws 50, 52 with additional angles 67, 69 allows for greater curvature in the distal portion 36 of the inserter needle 14 and results in a greater angular range of operation for the suture grasping device as a whole. The angles 67, 69 may be roughly equivalent, though it is preferred that angle 67 be greater than angle 69 to provide greater clearance between the jaws 50, 52 in the open position.

Figure 9:
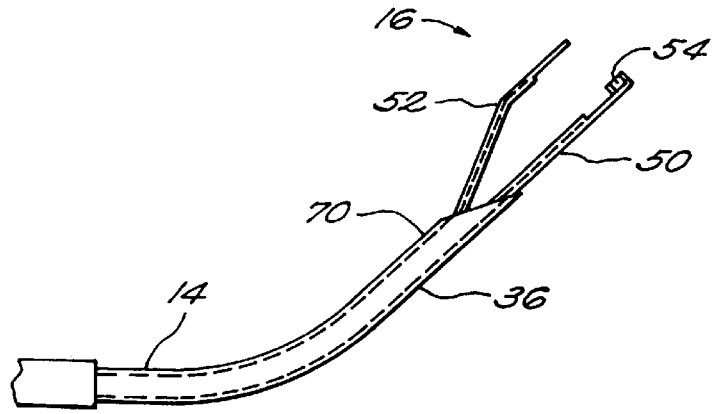
FIG. 9 is an elevated view of a distal portion of the suture retrograder of FIGS. 1–3 illustrating the suture grasping element in a fully extended, open position.
Figure 10:
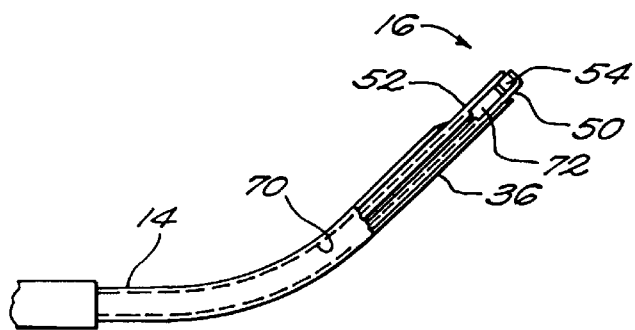
FIG. 10 is an elevated view, with a partial cut-away, of the distal end of the suture retrograder of FIG. 9, showing the suture grasping element in a partially retracted, intermediate position.

Referring again to FIG. 1, the suture grasping device 10 is shown with the suture grasping element 16 in the open, extended position. The actuator 18 is located in its second, or distal-most, position and the lining member 20, which connects the actuator 18 to the suture grasping element 16, is also in its distal-most position. Correspondingly, the suture grasping element 16 extends beyond the distal end 36 of the hollow introducer needle 14 in its open position as shown in FIG. 9.

When the suture grasping element 16 is fully extended, it extends approximately by a distance of about 0.250 to 0.500 inch beyond the distal end 36 of the introducer needle 14. The distance by which the element 16 extends may be varied by a person of ordinary skill in the art depending upon the circumstances under which the device of the invention is used. However, a preferred distance is about 0.375 inch when the actuator 18 is in the second, distal-most position.

As the actuator 18 is moved from the second, distal-most position toward the first, proximal-most position, the angled first segment 58 of the second jaw 52 contacts the inner wall 70 of the distal end 36 of the hollow introducer needle 14, and the second jaw 52 is forced towards the first jaw 50. As the actuator reaches an intermediate position, the second jaw 52 contacts the pod 54 on the first jaw 50 (shown in FIG. 10), thereby achieving a closed state and defining a region 72 between the jaws 50, 52 wherein a suture may effectively be retained. When the actuator 18 is in the intermediate position, the suture retaining region 72 extends beyond the distal end 36 of the introducer needle 14 by a distance of about 0.050 to 0.500 inch, and preferably about 0.125 inch, so that a retained suture may be slidably manipulated by the suture grasping device 10. The actual distance by which the element 16 extends may, of course, be varied by a person of ordinary skill in the art depending upon the circumstances under which the device of the invention is used.

When the actuator 18 is moved all of the way to its first, proximal-most position, the suture grasping element 16 is fully retracted within the distal end 36 of the introducer needle 14. The fully retracted position of the suture grasping element 16, and the suture grasping region 72, is best seen by reference to FIG. 11.

Figure 11:
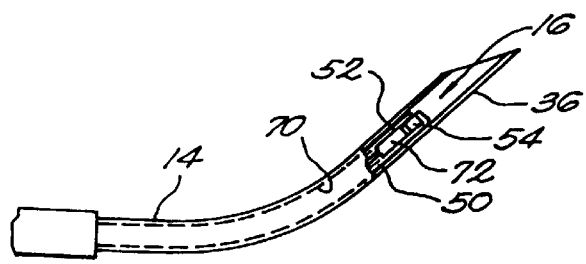
FIG. 11 is an elevated view, with a partial cut-away, of the distal end of the suture retrograder of FIG. 9, showing the suture grasping element in a fully retracted, closed position.
Figure 11A:
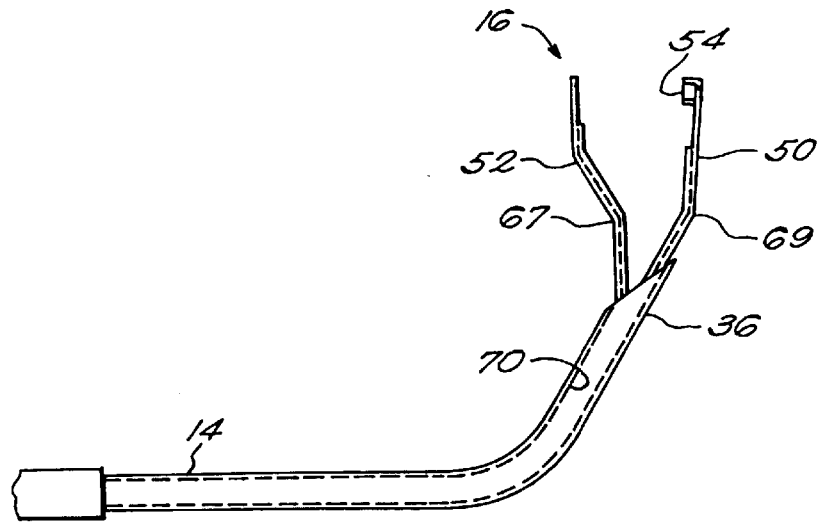
FIG. 11A is an elevated view of a distal portion of a suture retrograder of the invention having the suture grasping element of FIG. 8B in a fully extended, open position.
Figure 11B:
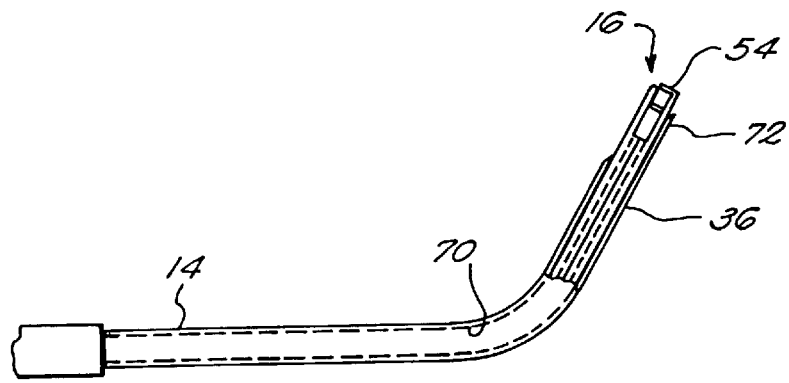
FIG. 11B is an elevated view, with a partial cut-away, of the distal end of the suture retrograder of FIG. 11A, showing the suture grasping element in a partially retracted, intermediate position.
Figure 11C:
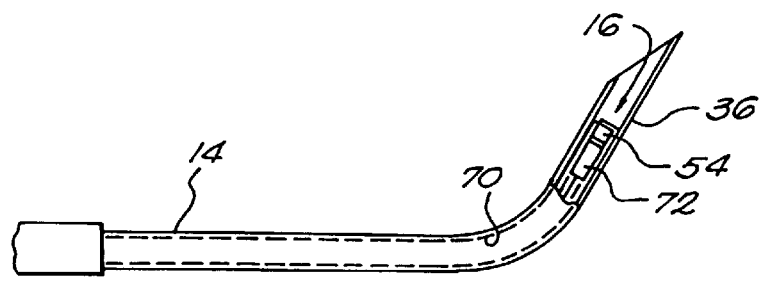
FIG. 11C is an elevated view, with a partial cut-away, of the distal end of the suture retrograder of FIG. 11A, showing the suture grasping element in a fully retracted, closed position.

The extended, intermediate and retracted positions of the suture grasping element 16 having additional angles 67, 69 (shown in FIG. 8B) are illustrated in FIGS. 11A, 11B and 11C, respectively.

Figure 12:
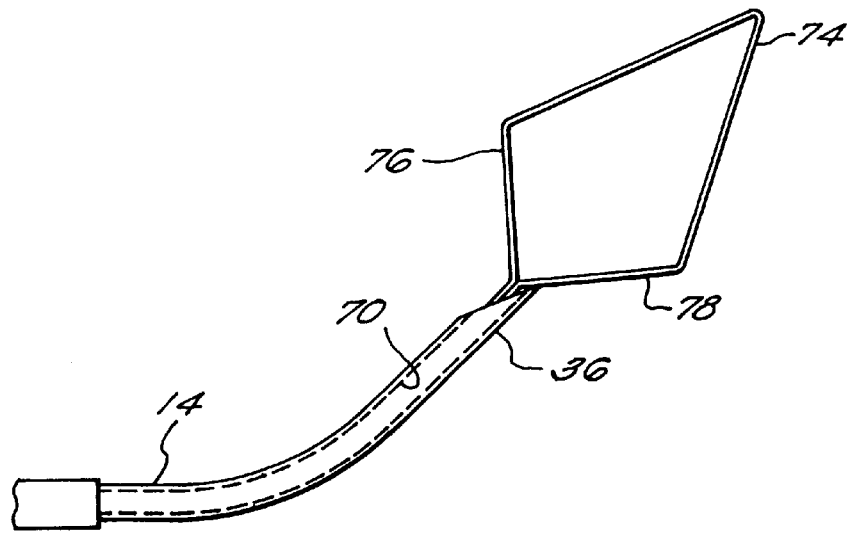
FIG. 12 is an elevated view of a distal portion of an alternative embodiment of the suture retrograder of the invention, illustrating a looped suture grasping element in a fully extended, open position.
Figure 13:
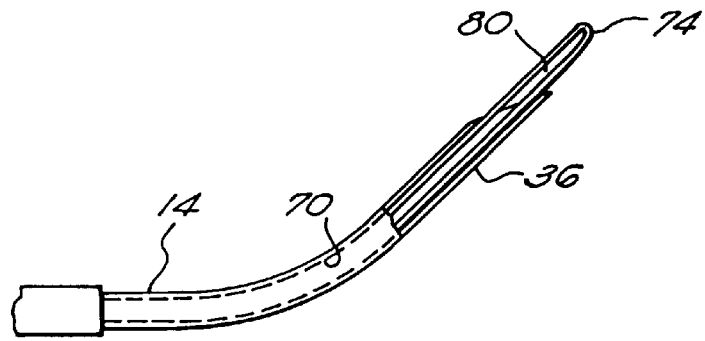
FIG. 13 is a perspective view, with a partial cut-away, of the embodiment of FIG. 12 showing the looped suture grasping element in a partially retracted, intermediate position.
Figure 14:
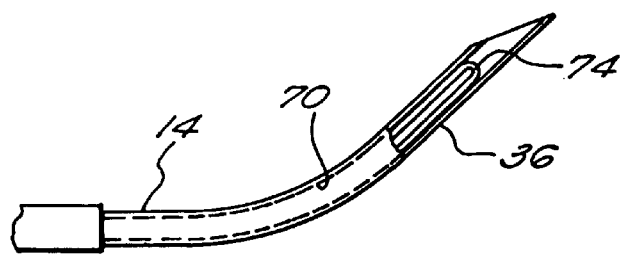
FIG. 14 is a perspective view, with a partial cut-away, of the embodiment of FIG. 12 showing the looped suture grasping element in a fully retracted, closed position.

The suture grasping device of the invention may utilize other suture grasping element configurations, such as the wire loop 74 suture grasping element shown in FIGS. 12–14. As with the two-jaw suture grasping element 16, the wire loop 74 may be made from a flexible material suitable for surgical use, including metals such as stainless steel or super elastic nickel-titanium (Nitinol) or plastic materials having elastic properties such as polyester, polypropylene or nylon. Preferably, the wire loop 74 is constructed from Nitinol. The wire loop 74 may be formed from a single, continuous wire element, or it may be formed using two wire elements joined at a distal portion of each.

The wire loop 74 of FIG. 12 has two leg segments 76, 78. Beginning at a proximal end of the wire loop 74 and moving distally, the leg segments diverge from one another, reach a point of maximum width there-between, then converge to meet at a distal end of the wire loop 74. The wire loop 74 thereby takes on a quadrangular or diamond shape when extended, as shown in FIG. 12. In its extended position, the wire loop 74 has a maximum width between the leg segments 76, 78 in the range of approximately 0.100 to 0.800 inch, and more preferably about 0.400 inch.

Like the two-jaw suture grasping element 16, the wire loop 74 may also be retracted to an intermediate position as shown in FIG. 13. As the actuator 18 is moved from its second or distal-most position to the intermediate position, the diverging portions of the two leg segments 76, 78 contact the inner wall 70 of the distal end 36 of the hollow introducer needle 14. This causes the quadrangular shaped wire loop 74 to compress, or fold up, as it is retracted into the introducer needle 14. When the actuator 18 reaches the intermediate position, a small portion of the wire loop 74 remains extended beyond the distal end 36 of the introducer needle 14 and thereby defines a region 80 within the loop 74 where a suture may be retained. The retained suture may then be manipulated by the suture grasping device 10. In this partially retracted position, the width of the wire loop 74 illustrated in FIG. 13 should be sufficient to slidably retain a suture within the wire loop 74. This width is generally in the range of about 0.020 to 0.250 inch, and more preferably is approximately 0.0675 inch. The loop 74 may generally extend approximately 0.0675 to 0.250 inch, and more preferably extends 0.125 inch.

Moving the actuator 18 to its first, proximal-most position fully retracts the wire loop 74 within the distal end 36 of the introducer needle 14 as shown in FIG. 14.

Figure 15:
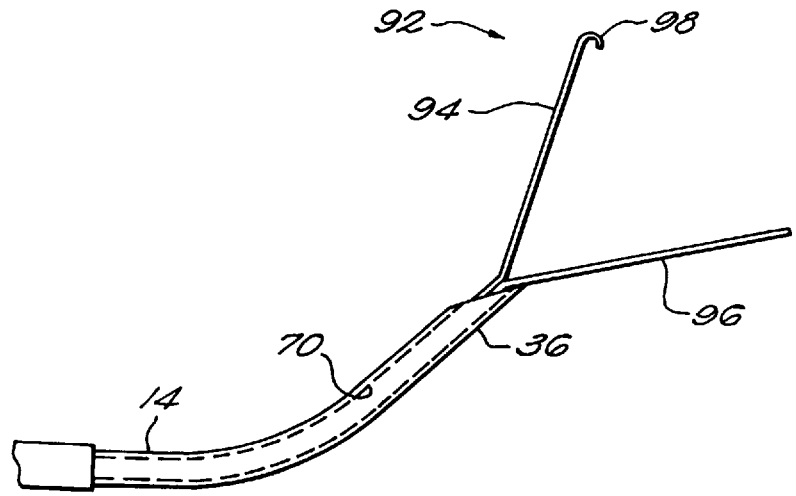
FIG. 15 is a perspective view of a distal portion of an additional embodiment of the suture retrograder of the invention, illustrating a suture grasping element having two wire-like members in a fully extended, open position.
Figure 16:
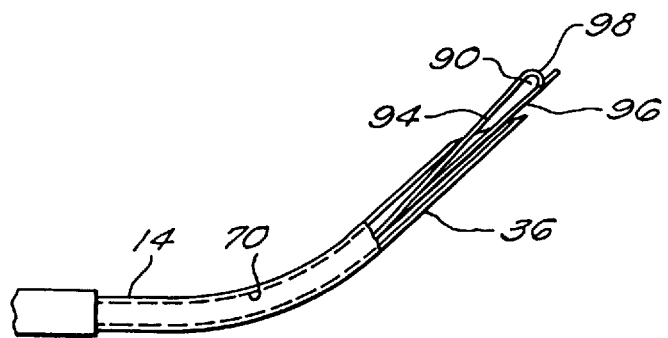
FIG. 16 is a perspective view, with a partial cut-away, of the embodiment of FIG. 15 showing the suture grasping element having two wire-like members in a partially retracted, intermediate position.
Figure 17:
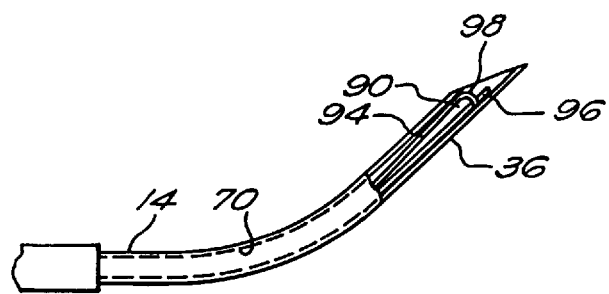
FIG. 17 is a perspective view, with a partial cut-away, of the embodiment of FIG. 15 showing the suture grasping element having two wire-like elements in a fully retracted, closed position.

The suture grasping device of the invention may also utilize a two member suture grasping element 92 as illustrated in FIGS. 15–17. The suture grasping element 92 consists of two wire-like members 94, 96. The first wire-like member 94 has a transverse hooked end 98 which is curved toward the second wire-like member 96, the curve being formed in a plane that is substantially transverse to the first wire-like member 94. In general, the hooked end 98 may be formed on either or both of the wire-like members 94, 96. FIG. 15 illustrates the two-member suture grasping element 92 in the fully extended, open position. In the illustrated embodiment, both wire-like members 94, 96 are flexible and articulatable. Preferably, the wire-like members are constructed from nickel-titanium (Nitinol). The spacing between the transverse hooked end 98 and the second wire-like member 96 in the open position is generally in the range of about 0.050 to 0.500 inch, and is preferably about 0.250 inch. Fully extended, the wire-like members 94, 96 extend a distance of about 0.250 to 0.500 inch beyond the distal end of the introducer needle 14. A preferred extension distance is about 0.375 inch.

The two-member suture grasping element 92 is shown in the partially retracted, intermediate position in FIG. 16. In this position, the hooked end 98 of the first wire-like member 94 contacts the second wire-like member, and creates a retaining region 90 between the two wire like members where a suture thread may be slidably retained. In this position, the suture retaining region 90 extends beyond the distal end 36 of the introducer needle 14 by a distance of about 0.050 to 0.500 inch, and preferably about 0.125 inch.

In the partially retracted position, the width of the suture retaking region 90 should be sufficient to slidably retain a suture between the wire-like members 94, 96. This width is generally in the range of about 0.020 to 0.250 inch, and more preferably is approximately 0.067 inch.

FIG. 17 illustrates the two member suture grasping element in the fully retracted, closed position.

Figure 18:
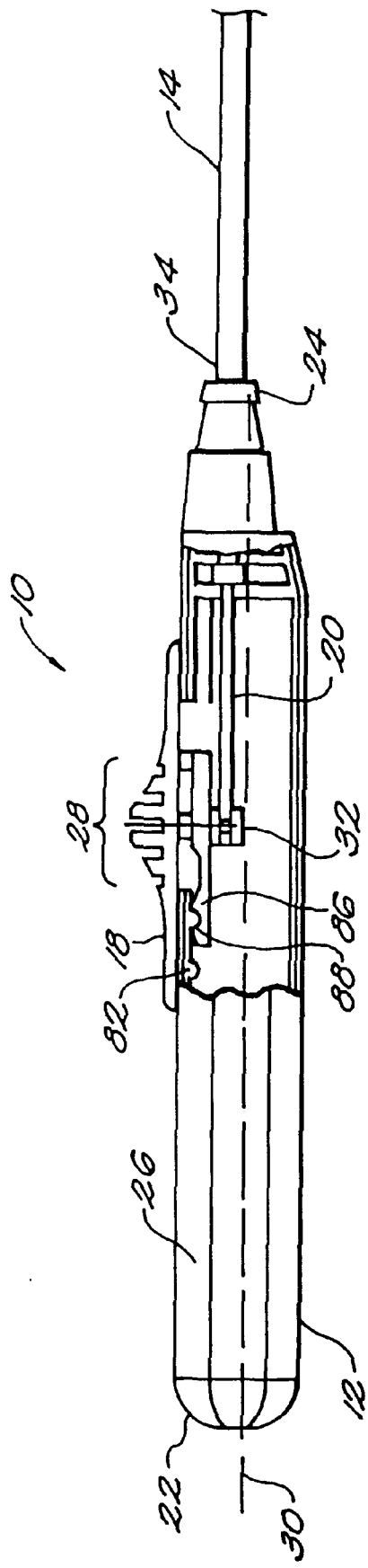
FIG. 18 is an elevated view with, with a partial cut-away, of a handle portion of the suture retrograder device of the invention.

Referring to FIG. 18, detents may be provided to lock the suture grasping device 10 in the fully retracted and intermediate positions. These detents may suitably be provided by forming protruberances 82, 84 on the interior of the housing 12 corresponding to the fully retracted and intermediate positions respectively. A biased member 86 attached to the transverse member 32 of the actuator 18 has a recess 88 which corresponds to the shape of the protruberances 82, 84. Accordingly, when the actuator 18 passes into the first or intermediate position, a detent is achieved.

It will be understood that the foregoing is only illustrative of the principles of the invention, and that various modifications can be made by those skilled in the art without departing form the scope and spirit of the invention. All references cited herein are expressly incorporated by reference in their entirety.

What is claimed is:

1. A suture grasping device, comprising:

an elongate housing having a proximal end, a distal end, a sidewall disposed between the proximal and distal ends and a longitudinal axis;

a hollow introducer needle having a proximal end attached to the distal end of the housing, and an open distal end having a tissue penetrating edge;

a suture grasping element disposed within the open distal end of the introducer needle, the suture grasping element being selectively movable between at least extended and retracted positions; and an actuator element slidably mounted on the sidewall of the housing, the actuator element being effective to move the suture grasping element between extended and retracted positions;

wherein the actuator element is movable among a first position in which the suture grasping element is fully retracted within the introducer needle, an intermediate position in which the suture grasping element is partially extended from the introducer needle and a second position in which the suture grasping element is fully extended from the introducer needle, and wherein a biased detent means is provided in the housing for releasably locking the actuator in at least the intermediate position.

2. The device of claim 1, wherein the introducer needle and the housing are at least partially coaxial.

3. The device of claim 1, wherein the biased detent means releasably locks the actuator element in at least the first and intermediate positions.

4. The device of claim 1, wherein the suture grasping element comprises:

a first jaw having a pod located on a distal end thereof, and an articulatable second jaw movable between a closed position wherein a distal portion of the second jaw contacts the pod element on the first jaw in a manner sufficient to retain a suture between the jaws, and an open position wherein the second jaw is spaced apart from the first jaw.

5. The device of claim 4, wherein when the actuator element is in the intermediate position, the suture grasping element is partially extended from the introducer needle and the second jaw is in the closed position, and when the actuator element is in the second position, the suture grasping element is fully extended from the introducer needle and the second jaw is in the open position.

6. The device of claim 4, wherein the second jaw is biased to the open position.

7. The device of claim 4, wherein the first jaw is substantially straight, and the second jaw consists of at least two segments including a first segment forming an angle of between about 15° and 45° with the first jaw, and a second segment, that is distal to the first segment, substantially parallel to the first jaw and spaced apart from the first jaw.

8. The device of claim 1, wherein the suture grasping element comprises a wire loop having at a proximal end two leg segments that diverge from one another and then converge to meet one another at a distal end thereof, the suture grasping element substantially forming a diamond shape when the suture grasping element is fully extended.

9. The device of claim 8, wherein the suture grasping element is made from a deformable material that is able to be compressed to fit within the inner bore of the hollow introducer needle in the retracted position and to expand to the substantially diamond-shaped configuration when in the extended position.

10. The device of claim 1, wherein the suture grasping element comprises a first wire-like member having a transverse hook and a second wire-like member.

11. The device of claim 10, wherein the first and second wire-like elements are spaced apart in the fully extended position, and the transverse hook contacts the second wire-like element in the intermediate, partially extended position in a manner sufficient to retain a suture between the first and second wire-like elements.

12. A suture grasping device, comprising:
   a hollow housing having a proximal end, a distal end, a sidewall disposed between the proximal and distal ends and a longitudinal axis;
   a hollow introducer needle having an inner bore, a proximal end attached to the distal end of the housing, and an open distal end having a sharpened edge;
   a suture grasping element disposed within the inner bore and being selectively movable between at least extended and retracted positions, the suture grasping element having first and second jaw components at least one of which includes a pod member on a distal end thereof; and
   an actuator element slidably mounted on the housing, the actuator being slidable between at least first and second positions to effect retraction and extension of the suture grasping element.

13. The device of claim 12, wherein first and second jaw components are formed from a single tubular element.

14. The device of claim 13, wherein the pod is formed from a folded portion of the tubular element.

15. The device of claim 12, wherein the second jaw is movable between a closed position, wherein the distal ends of the jaws make contact in a manner sufficient to retain a suture between the jaws, and an open position wherein the jaws are spaced apart.

16. The device of claim 15, wherein the jaws extend about 0.25 to 0.50 inch beyond the distal end of the introducer needle when the actuator is in the second position.

17. The device of claim 15, wherein the jaws are spaced apart about 0.02 to 0.25 inch in the open position.

18. The device of claim 15, wherein the second jaw is biased to the open position.

19. The device of claim 15, wherein the first jaw is substantially straight, and the second jaw consists of at least two linear segments including a first segment forming an angle of between about 15° and 45° with the first jaw, and a second segment that is distal to the first segment, substantially parallel to and spaced apart from the first jaw.

20. The device of claim 14, wherein the actuator further includes an intermediate position, located between the first and second positions that places the second jaw is in the closed position such that second jaw contacts the first jaw at a distance away from the distal end of the introducer needle.

21. The device of claim 14, wherein the first and second jaws are angled, both in the same direction.

22. The device of clam 20, wherein the jaws extend about 0.10 to 0.30 inches beyond the distal end of the introducer needle when the actuator is in the intermediate position.

23. The device of claim 20, wherein when the actuator is moved from the second position to the intermediate position, the first, angled segment of the second jaw contacts the inner bore of the introducer needle, and the second jaw is thereby moved from the open position to the closed position.

24. The devices of claim 12, wherein a recessed region, suitable for retaining a suture, is provided on the first jaw proximally adjacent to each pod.

25. The device of claim 12, wherein the distal end of the introducer needer is disposed at an angle with respect to the proximal end of the introducer needle.

26. The device of claim 12, wherein the distal end of the introducer needle forms a hook.

\* \* \* \* \*